United States Patent [19] [11] Patent Number: 5,811,611
Hamamatsu et al. [45] Date of Patent: Sep. 22, 1998

[54] METHOD FOR PRODUCING MONOALKENYL BENZENE

[75] Inventors: Tatsuo Hamamatsu, Kawasaki; Mitsuo Matsuno, Yokohama, both of Japan

[73] Assignee: Nippon Oil Co., Ltd., Tokyo, Japan

[21] Appl. No.: 702,740

[22] Filed: Aug. 23, 1996

[30] Foreign Application Priority Data

Aug. 30, 1995 [JP] Japan ................................. 7-221454

[51] Int. Cl.$^6$ ........................................................ C07C 15/42
[52] U.S. Cl. ............................................................ 585/438
[58] Field of Search ........................... 585/438, 452, 585/467, 468, 435

[56] References Cited

U.S. PATENT DOCUMENTS 5,436,381 7/1995 Takagawa et al. ....................... 585/452
5,444,172 8/1995 Takagawa et al. ....................... 585/452
5,527,977 6/1996 Takagawa et al. ....................... 585/452

FOREIGN PATENT DOCUMENTS 5112476  5/1993  Japan .

Primary Examiner—Walter D. Griffin
Assistant Examiner—Thuan D. Dang
Attorney, Agent, or Firm—Darby & Darby

[57] ABSTRACT

A method for producing a monoalkenyl benzene including reacting an alkyl benzene having 7 to 10 carbon atoms with a conjugated diene compound having 4 to 6 carbon atoms in the presence of a particular catalyst. The particular catalyst is obtained by depositing at least one of sodium, potassium, sodium amide, and potassium amide on a support made of a compound represented by the formula of $K_2O \cdot xAl_2O_3$ wherein x is $0.5 \leq x \leq 11$, to obtain a precursor of a catalyst, and contacting the precursor of a catalyst with at least one of water, an alcohol, and a phenol. The precursor of the catalyst may be contacted with hydrogen before contacted with at least one of water, an alcohol, and a phenol.

18 Claims, No Drawings

METHOD FOR PRODUCING MONOALKENYL BENZENE

BACKGROUND OF THE INVENTION

This invention relates to a method for producing a monoalkenyl benzene, and more particularly to a method for producing a monoalkenyl benzene employed as a precursor for pharmaceuticals, agricultural chemicals, or polymer materials.

There has hitherto been known a method for producing a monoalkenyl benzene by reacting an alkyl benzene with a conjugated diene such as 1,3-butadiene, in the presence of an alkali metal catalyst, and the monoalkenyl benzene has been known to be useful as a precursor for pharmaceuticals, agricultural chemicals, or polymer materials (German Patent No. 557514). However, this known method has a yield of 30% at most and hence is inconvenient for practicing industrially.

There has also been proposed a method in which an oxide of an alkali metal or an alkaline earth metal such as calcium oxide, is employed as a catalyst for improving the above method (U.S. Pat. No. 3,244,758). However, this catalyst has a prolonged induction period, in other words, a lot of time is required until the maximum activity is achieved, i.e. until a steady state of the reaction is reached, thus raising problems in connection with economic profitability and operational safety.

With the above methods, not only a monoalkenyl benzene but also compounds in which a conjugated diene is further added to the monoalkenyl benzene or higher molecular compounds are produced simultaneously, and these polymers covering the catalyst surface gradually deactivate the catalyst. Particularly, in using such catalyst, not only the activity but also the selectivity tends to decline. Such catalyst is solidified by a resinous polymers within the reactor, but the catalyst is not completely deactivated and still contains active parts, so that when the used catalyst is taken out for exchange, it is likely to be ignited due to contact with oxygen and moisture in the atmosphere to cause fire, thus raising difficulties in handling.

In order to solve these problems, the present inventors have proposed a method in which a catalyst obtained by depositing sodium and/or sodium amide on a support having the composition represented by the formula of $K_2O.xAl_2O_3$ is employed (Japanese Laid-open Patent Application No. 7-82178). According to this method, not only the problems raised in the conventional methods using a variety of catalysts can be solved, but also the reaction speed and the product selectivity to a monoalkenyl benzene can be improved remarkably, and the high activity and the high selectivity can be maintained for an extremely long time. However, a method in which still higher selectivity is achieved is demanded.

SUMMARY OF THE INVENTION

It is an object of the present invention to provide a method for producing a monoalkenyl benzene in which the induction period of the catalyst is shortened, and by which an object compound can be produced with higher selectivity and higher yield.

The present inventors have made intensive studies of the conventional methods and catalysts to find an unexpected method for improving the method for producing a monoalkenyl benzene as will be discussed below to reach the present invention.

It has been known that an alkali metal or an organic alkali metal compound easily reacts with water or alcohols upon contacting the same to convert to a hydroxide or an alkoxide to lose its catalyst activity. Thus, the contact of an alkali metal or an organic alkali metal compound with water or alcohols is avoided. However, the present inventors have found that, surprisingly, when a monoalkenyl benzene is produced by reacting an alkyl benzene with a conjugated diene compound in the presence of a catalyst obtained by depositing at least one of sodium, potassium, sodium amide, and potassium amide on a support having the composition represented by the formula of $K_2O.xAl_2O_3$ to obtain a precursor of a catalyst and contacting the precursor of a catalyst with at least one of water, an alcohol, and a phenol, the catalyst activity is not at all declined but improved, and the monoalkenyl benzene selectivity is remarkably improved.

Further, the inventors have found that, by contacting the precursor of a catalyst with hydrogen before it is contacted with water, an alcohol or a phenol, shortening of the induction period, in addition to the improvement in activity and monoalkenyl benzene selectivity, can be achieved.

Therefore, according to the present invention, there is provided a method for producing a monoalkenyl benzene comprising reacting an alkyl benzene having 7 to 10 carbon atoms with a conjugated diene compound having 4 to 6 carbon atoms in the presence of a catalyst obtained by depositing at least one of sodium, potassium, sodium amide, and potassium amide on a support consisting essentially of a compound represented by the formula of $K_2O.xAl_2O_3$ wherein x is $0.5 \leq x \leq 11$, to obtain a precursor of a catalyst, and contacting said precursor of a catalyst with at least one of water, an alcohol, and a phenol.

PREFERRED EMBODIMENTS OF THE INVENTION

The present invention will be explained hereinbelow in detail.

In the method of the present invention, a particular catalyst is used. For producing the particular catalyst, a support consisting essentially of a compound represented by the formula of $K_2O.xAl_2O_3$ wherein x is $0.5 \leq x \leq 11$, preferably $0.7 \leq x \leq 10$ (referred to as "support (1)" hereinbelow) is used. In the support (1) of the present invention, the support consisting essentially of a compound represented by the formula of $K_2O.xAl_2O_3$ indicates that the support (1) is basically made up of $K_2O.xAl_2O_3$ as its component, and represents, for convenience sake, the composition of a support (1) in case of changes in the ratio of raw materials of the support as will be explained later. That is, the above formula does not mean that the compound $K_2O.xAl_2O_3$ remains as such in the support (1) but are present in the form of a double oxide. Consequently, the support (1) is not a simple mixture of $K_2O$ and $xAl_2O_3$ and the favorable effects of the present invention cannot be achieved with the use of such simple mixture.

There is no particular limitation to the method for preparing the support (1), and the support (1) may be prepared by contacting a potassium-containing compound with an aluminum-containing compound.

The potassium-containing compound may preferably be a compound forming a potassium oxide by calcination. Examples of the potassium-containing compound may include potassium hydroxide, potassium hydrogen carbonate, potassium carbonate, potassium hydride, potassium acetate, and compounds represented by the formula $KR^1$ or $KOR^2$, wherein $R^1$ and $R^2$ stand for straight or branched aliphatic hydrocarbon residues having 1 to 20, preferably 1 to 8 carbon atoms, or aryl or aralkyl groups having 6 to 30, preferably 6 to 12 carbon atoms. Specifically, $R^1$ and $R^2$ may stand for alkyl groups such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, dodecyl, or hexadecyl groups; alkenyl groups such as vinyl or allyl groups; aryl groups such as phenyl, tolyl, xylyl, cumenyl, or ethylphenyl groups; or aralkyl groups such as benzyl, dimethyl benzyl or phenethyl groups.

Preferable examples of the potassium-containing compound represented by the formula of $KR^1$ may include methylpotassium, vinylpotassium, ethylpotassium, phenylpotassium, tolylpotassium, benzylpotassium, dodecylpotassium, hexadecylpotassium, dimethyl benzylpotassium, and phenyl ethylpotassium. Preferable examples of the potassium-containing compound represented by the formula of $KOR^2$ may include ethoxypotassium, butoxypotassium, and isopropoxypotassium. These potassium-containing compounds may contain hydrates and may be used alone or in mixture.

When potassium carbonate is used as the potassium-containing compound, excess potassium carbonate may remain unreacted in the support (1).

In other words, the support (1) used in the present method may be made up of $K_2O \cdot xAl_2O_3$ alone, or of $K_2O \cdot xAl_2O_3$ as the main component with a minor amount of residual unreacted potassium carbonate used as the raw material for preparing the support (1). In the latter case, the residual amount of potassium carbonate may preferably be not more than 30 parts by weight based on 100 parts by weight of $K_2O \cdot xAl_2O_3$.

Examples of the aluminum-containing compound may include alumina hydrates such as hydrargillite, nordstrandite, bayerite, boehmite, or diaspore; aluminas such as $\alpha$-alumina, $\theta$-alumina, $\kappa$-alumina, $\delta$-alumina, $\eta$-alumina, $\gamma$-alumina, $\chi$-alumina, and $\rho$-alumina; and aluminum-containing compounds represented by the formula of $Al(OR^3)_3$ wherein $R^3$ stands for a straight or a branched aliphatic hydrocarbon residue having 1 to 20, preferably 1 to 8 carbon atoms, or an aryl or an aralkyl group having 6 to 30, preferably 6 to 12 carbon atoms. Specifically, $R^3$ may stand for an alkyl group such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, dodecyl, or hexadecyl group; an alkenyl group such as vinyl or allyl group; an aryl group such as phenyl, tolyl, xylyl, cumenyl, or ethylphenyl group; or an aralkyl group such as benzyl, dimethyl benzyl or phenethyl group.

Examples of the aluminum-containing compound represented by the formula of $Al(OR^3)_3$ may include trimethoxy aluminium, triethoxy aluminum, tripropoxy aluminum, triisopropoxy aluminum, tributoxy aluminum, triisobutoxy aluminum, tri-sec-butoxy aluminum, tri-tert-butoxy aluminum, tripentyloxy aluminum, triisopentyloxy aluminum, trineopentyloxy aluminum, tri-tert-pentyloxy aluminum, trihexyloxy aluminum, triisohexyloxy aluminum, triheptyloxy aluminum, trioctyloxy aluminum, triphenoxy aluminum, and tribenzyloxy aluminum.

The potassium-containing compound may be contacted with the aluminum-containing compound by mixing the potassium-containing compound and the aluminum-containing compound so that K/Al ratio in the formula of $K_2O \cdot xAl_2O_3$ is $0.5 \leq x \leq 11$, calcining, and grinding and classifying the obtained aggregates.

The potassium-containing compound may also be contacted with the aluminum-containing compound by kneading the potassium-containing compound and the aluminum-containing compound together, extruding or compression molding the resulting mixture to form pellets, and calcining the pellets.

There is no particular limitation to the conditions of the calcination, but it is preferred to effect the calcination in the presence or absence of air or nitrogen at a temperature of 400° to 2000° C., preferably 500° to 1500° C. for 1 to 20 hours, preferably 2 to 10 hours.

The shape of the support (1) is not particularly limited, and may suitably be selected depending on the shape or capacity of the reactor or conditions of the reaction. Preferable shape of the support (1) is in the form of powders or pellets, and preferable particle size is 0.1 to 10 mm.

For preparing the particular catalyst employed in the method of the present invention, first at least one of sodium, potassium, sodium amide, and potassium amide (referred to as "component (2)" hereinbelow) is deposited on the support (1) to obtain a precursor of the catalyst.

The amount of the component (2) supported on the support (1) is preferably 0.1 to 30 parts by weight, more preferably 1 to 20 parts by weight in terms of sodium atoms or potassium atoms in the component (2) based on 100 parts by weight of the support (1). If the amount of the component (2) supported on the support (1) is less than 0.1 parts by weight, sufficient activity is hard to obtain. On the other hand, even if the amount of the component (2) supported on the support (1) is more than 30 parts by weight, the activity does not tend to be improved any more, and thus the amount of the component (2) is usually within the above-mentioned range.

Among the component (2), sodium and/or potassium may be deposited on the support (1) by agitating and mixing the support (1) and sodium and/or potassium together at 120° to 400° C. for 30 minutes to 10 hours in the absence of a solvent; by depositing sodium and/or potassium vapor on the support (1); or by agitating and mixing sodium and/or potassium and the support (1) together at a high speed in a high-boiling solvent such as white oil at 120° to 400° C.

On the other hand, among the component (2), sodium amide and/or potassium amide may be deposited on the support (1) by dissolving sodium and/or potassium in liquid ammonia to form an ammonia solution of sodium amide and/or potassium amide, immersing the support (1) in the thus obtained ammonia solution at a temperature of preferably 0° to 200° C. for usually 30 minutes to 10 hours, and vaporizing off ammonia. If sodium and/or potassium and sodium amide and/or potassium amide are to be deposited on the support (1) together, one or more of the above methods may be selected and combined in any suitable manner.

For preparing the particular catalyst employed in the method of the present invention, after depositing the component (2) on the support (1) to obtain the precursor of the catalyst, the precursor of the catalyst is contacted with component (3) as discussed later, thereby obtaining the particular catalyst. Alternatively, the precursor of the catalyst may be contacted with hydrogen before it is contacted with the component (3), thereby obtaining the particular catalyst with shorter induction period. In other words, the time required for achieving a steady state of the catalytic reaction can be shortened. The precursor of the catalyst obtained by depositing the component (2) on the support (1) may be contacted with hydrogen, for example, at 0° to 400° C. under the pressure of 0° to 100 kg/cm².G for 30 minutes to 10 hours.

For preparing the particular catalyst employed in the method of the present invention, the precursor of the catalyst obtained by depositing the component (2) on the support (1), or the precursor of the catalyst obtained by depositing the component (2) on the support (1), which precursor has been contacted with hydrogen, is contacted with at least one of water, an alcohol, and a phenol (referred to as "component (3)" hereinbelow), thereby obtaining the particular catalyst.

Examples of the alcohol in the component (3) may include monohydric alcohols, dihydric alcohols, and trihydric alcohols.

The monohydric alcohol is a compound represented by the formula of $R^4OH$, wherein $R^4$ may stand for a straight or a branched primary, secondary, or tertiary alkyl group having 1 to 11 carbon atoms such as methyl, ethyl, propyl, butyl, pentyl, hexyl, heptyl, octyl, nonyl, decyl, or undecyl group; a straight or a branched primary, secondary, or tertiary alkenyl group having 2 to 11 carbon atoms; or a straight or a branched primary, secondary, or tertiary aralkyl group having 7 to 21 carbon atoms such as benzyl, α-methyl benzyl, or phenethyl group. Examples of the monohydric alcohol may include methanol, ethanol, 1-propanol, 2-propanol, 1-butanol, 2-butanol, 2-methyl-1-propanol, 2-methyl-2-propanol, 1-pentanol, 2-pentanol, 3-pentanol, 1-hexanol, 1-heptanol, 1-octanol, benzyl alcohol, α-methylbenzyl alcohol, and phenethyl alcohol.

The dihydric alcohol may be a compound represented by the formula of $R^5CH(OH)CH_2(OH)$, wherein $R^5$ may stand for a hydrogen atom; a straight or a branched primary, secondary, or tertiary alkyl group having 1 to 10 carbon atoms such as methyl, ethyl, propyl, butyl, pentyl, hexyl, heptyl, octyl, nonyl, or decyl group; a straight or a branched primary, secondary, or tertiary alkenyl group having 2 to 10 carbon atoms; an aryl group having 6 to 20 carbon atoms such as phenyl, tolyl, xylyl, cumenyl, mesityl, or naphthyl group; or a straight or a branched primary, secondary, or tertiary aralkyl group having 7 to 20 carbon atoms such as benzyl, a-methylbenzyl, or phenethyl group. Examples of the dihydric alcohol may include ethylene glycol and propylene glycol.

The trihydric alcohol may be a compound represented by the formula of $R^5CH(OH)CH(OH)CH_2(OH)$, wherein $R^6$ may stand for a hydrogen atom; a straight or a branched primary, secondary, or tertiary alkyl group having 1 to 10 carbon atoms such as methyl, ethyl, propyl, butyl, pentyl, hexyl, heptyl, octyl, nonyl, or decyl group; a straight or a branched primary, secondary, or tertiary alkenyl group having 2 to 10 carbon atoms; an aryl group having 6 to 20 carbon atoms such as phenyl, tolyl, xylyl, cumenyl, mesityl, or naphthyl group; or a straight or a branched primary, secondary, or tertiary aralkyl group having 7 to 20 carbon atoms such as benzyl, α-methylbenzyl, or phenethyl group. Example of the trihydric alcohol may include glycerol.

The phenol is a compound represented by the formula of R7OH, wherein $R^7$ may stand for an aryl group having 6 to 20 carbon atoms such as phenyl, tolyl, xylyl, cumenyl, mesityl, or naphthyl group. Examples of the phenol may include phenol, cresol, and naphthol.

The compounds listed above as the component (3) may be used alone or in mixture.

Among the compounds listed above as the component (3), water, methanol, ethanol, 1-propanol, 2-propanol, ethylene glycol, and phenol are particularly preferred.

The amount of the component (3) to be contacted with the precursor of the catalyst or the precursor of the catalyst contacted with hydrogen is preferably 0.1 to 200 mol %, more preferably 1 to 100 mol % of the component (2) in the precursor of the catalyst or the precursor of the catalyst contacted with hydrogen. If the amount of the component (3) to be contacted is less than 0.1 mol %, the selectivity of the catalyst to be obtained may not be improved sufficiently, thus being not preferred.

The precursor of the catalyst or the precursor of the catalyst contacted with hydrogen may be contacted with the component (3) in a liquid hydrocarbon as a solvent. For example, the precursor of the catalyst or the precursor of the catalyst contacted with hydrogen may be contacted with the component (3) by dissolving the component (3) in a liquid hydrocarbon, introducing the precursor of the catalyst or the precursor of the catalyst contacted with hydrogen in the form of powders or pellets into the resulting solution, and agitating the mixture; or by immersing the precursor of the catalyst or the precursor of the catalyst contacted with hydrogen in the form of powders or pellets in a liquid hydrocarbon in advance, and adding thereto a liquid hydrocarbon solution of the component (3) under agitation. The liquid hydrocarbon may preferably has a boiling point equal to or higher than that of heptane. Examples of the liquid hydrocarbon may include heptane, octane, nonane, decane, undecane, dodecane, decalin, toluene, ethylbenzene, xylene, diethylbenzene, trimethylbenzene, cumene, ethyldimethylbenzene, and cymene. The contacting temperature is preferably −10° to 50° C., and the contacting time is preferably 10 minutes to 10 hours. In these methods, since the component (2) supported on the support (1) or the component (2) supported on the support (1) which has been contacted with hydrogen is extremely highly reactive with the component (3), the concentration of the component (3) should be sufficiently low so that local excess reaction will not occur. The concentration of the component (3) is preferably 0.005 to 10% by weight, more preferably 0.01 to 5% by weight of the liquid hydrocarbon as the solvent.

The catalyst used in the method of the present invention has properties such as superior dispersibility without aggregates, high activity and selectivity, and substantially no induction period at the beginning of the reaction, so that the catalyst is suitable not only for batch mode reaction or semi-batch mode reaction with continuous charge of starting materials, but also for complete mixing mode of reaction wherein both catalyst and starting materials are continuously charged into a stirring tank reactor. Further, the support (1) may be formed into a pellet with higher strength, compared to conventional catalysts such as potassium carbonate. Such support in the form of pellets can absorb and support a lot of sodium or potassium, hydrides thereof, or amides thereof very rapidly like the support in the form of powders. Therefore, the use of such support in the form of pellets in the method of the present invention is suitable for a method for production utilizing continuous flow mode of reaction using a fixed bed.

According to the present method for producing a monoalkenyl benzene, an alkyl benzene having 7 to 10 carbon atoms is reacted with a conjugated diene compound having 4 to 6 carbon atoms in the presence of the particular catalyst.

The alkyl benzene having 7 to 10 carbon atoms is a compound wherein hydrogen atoms on a benzene ring are substituted for at least one, preferably 1 to 4 alkyl groups. The alkyl groups may preferably be methyl groups, ethyl groups, or isopropyl groups.

Examples of the alkyl benzene may preferably include toluene, ethyl benzene, xylene, diethyl benzene, trimethyl benzene, cumene, ethyldimethyl benzene, cymene, and tetramethyl benzene. The alkyl benzene includes any substitution isomers thereof, if any. Among the specific examples of the alkyl benzene, oxylene, m-xylene, and p-xylene are particularly preferred. The alkyl benzene may be used alone or in mixture.

Examples of the conjugated diene compound may include 1,3-butadiene, isoprene, 1,3-pentadiene, 2,3-dimethyl butadiene, 2-ethyl butadiene, 2-methyl-1,3-pentadiene, 3-methyl-1,3-pentadiene, 4-methyl-1,3-pentadiene, 1,3-hexadiene, and 2,4-hexadiene. Any cis and trans thereof may be used, if any. The conjugated diene compound may be used alone or in mixture.

The alkyl benzene and the conjugated diene compound are not required to be of high purity. Thus it is only sufficient if compounds other than the object compound, such as olefins, diolefins, alkyl benzenes, water or a carbon dioxide gas, are removed to the industrially feasible usual level.

According to the method of the present invention, for example, the reaction between toluene and 1,3-butadiene synthesizes 5-phenylpentene-2, the reaction between o-xylene and 1,3-butadiene synthesizes 5-(o-tolyl) pentene-2, the reaction between o-xylene and 1,3-pentadiene synthesizes 1-(o-tolyl) hexene-3 and 4-methyl-5-(o-tolyl) pentene-2, the reaction between p-xylene and 1,3-butadiene synthesizes 5-(p-tolyl) pentene-2, the reaction between m-xylene and 1,3-butadiene synthesizes 5-(m-tolyl) pentene-2, and the reaction between ethyl benzene and 1,3-butadiene synthesizes 5-(phenyl) hexene-2.

The mixing ratio of the alkyl benzene to the conjugated diene compound for reaction is preferably 1:0.001 to 0.5, more preferably 1:0.01 to 0.4 in molar ratio.

The reaction between the alkyl benzene and the conjugated diene compound in the presence of the particular catalyst may preferably be carried out, as discussed above, in a batch mode using an autoclave, in a semi-batch mode with continuous charge of starting materials, in a complete mixing continuous mode in a bath-type reactor wherein the catalyst and the starting materials, i.e. the alkyl benzene and the conjugated diene are continuously charged, or in a continuous flow mode using a fixed bed wherein the starting material, i.e. the alkyl benzene and the conjugated diene are passed through the reactor charged with the catalyst in the form of pellets.

With the present invention, conditions of the reaction between the alkyl benzene and the conjugated diene compound in the presence of the particular catalyst may suitably be selected depending on the amount of the catalyst to be used and the charging amount. However, the reaction temperature is preferably 80°0 to 200° C., more preferably 100° to 180° C. The reaction time for the batch mode reaction or semi-batch mode reaction, or the residence time for the continuous mode reaction is preferably 5 minutes to 10 hours, more preferably 10 minutes to 5 hours. Further, for the continuous flow mode reaction using a fixed bed, the liquid hourly space velocity (LHSV) is preferably within the range of 0.1 to 10 (V/V.hr). The pressure during the reaction is preferably 5 to 200 kgf/cm$^2$, more preferably 10 to 100 kgf/cm$^2$.

In the method of the present invention, the amount of the particular catalyst used is not particularly limited. For example, when an autoclave is employed, the amount of the particular catalyst is preferably 0.5 to 20 parts by weight, more preferably 1 to 15 parts by weight based on 100 parts by weight of the alkyl benzene.

In the above reaction, a solvent may be used as long as it does not prevent the reaction. Examples of the solvent may include inert hydrocarbon compounds such as hexane, heptane, or benzene.

In the method of the present invention, after the reaction is finished, the objective monoalkenyl benzene can be obtained easily at a high yield by removing the unreacted substances by distillation or trapping.

The method for producing a monoalkenyl benzene of the present invention, compared to the conventional methods using a variety of catalysts, can provide high yield, maintain high activity and selectivity of the catalyst for a prolonged time, and are superior in economical profitability and in operational safety. Further, compared to the methods using a catalyst prepared by the conventional method without contacting the catalyst with the component (3) of the present invention, the product selectivity can be remarkably improved, and the risk of ignition and fire is eliminated. Therefore, the method of the present invention is useful as a method for industrially producing monoalkenyl benzenes.

EXAMPLES OF THE INVENTION

The present invention will now be described with reference to Examples and Comparative Examples. These embodiments are, however, given only by way of illustration, and are not intended for limiting the invention.

Example 1

66g of potassium hydroxide (containing 15 wt % of moisture) ground into fine powders and 60 g of boehmite were mixed thoroughly, charged in an alumina crucible, and calcined in an air atmosphere at 1200° C. for 5 hours. After the calcined product is allowed to cool, the product is taken out and ground in a centrifugal ball mill for 2 hours, and the powdered product having the particle size of less than 60 mesh were selected and used as a support. This support had the composition of $K_2O.0.98Al_2O_3$.

60 g of the support thus obtained were charged into a three-necked flask of 300 ml capacity and heated to 150° C. under a nitrogen gas atmosphere. To the heated mass were added 6 g of sodium under agitation. After the end of the addition, the temperature was raised to and maintained at 200° C. and agitation was continued for 1 hour to give a precursor of a catalyst. 100 g of o-xylene were charged into a well dried beaker of 500 ml capacity under a nitrogen atmosphere, and 580 mg of ethanol was added to obtain a solution. To this solution thus obtained, 16 g of the precursor of the catalyst was introduced, and agitated for 30 minutes. After the solution was removed by decantation, the obtained product was washed five times with a total of 200 ml of o-xylene, thereby obtaining a catalyst. In this operation, the amount of ethanol equivalent to 20 mol % of introduced sodium was consumed in the contacting reaction.

After a stainless steel autoclave with magnetic stirrer of 1000 ml capacity was dried and had its atmosphere thoroughly replaced by nitrogen, the catalyst obtained through the above operation in its entirety, 425 g of o-xylene, and 43 g of 1,3-butadiene were introduced into the autoclave and reacted at 140° C. for two hours. After the reaction, the reaction system was cooled to 100° and 1,3-butadiene which remained unreacted was collected by a trap in a dry ice-methanol bath. Unreacted o-xylene and reaction products remaining in the reactor were recovered by vacuum distillation. 1.8 g of 1,3-butadiene were recovered, while 455 g of a liquid product were recovered by vacuum distillation. Analysis by gas chromatography revealed that 116 g of 5-(o-tolyl) pentene-2 were produced. The yield was thus 91%.

Example 2

43 g of 1,3-butadiene and 425 g of o-xylene were charged into the autoclave in a reduced-pressure state employed in Example 1 and reacted at 140° C. for 1 hour. The reaction was discontinued since a pressure gauge of the autoclave indicated zero atmosphere and the residual 1,3-butadiene quantity was determined to be substantially zero. Post-treatment was carried out in the same way as in Example 1. 1 g of 1,3-butadiene was recovered, while 458 g of a liquid product were recovered. Further, 120 g of 5-(o-tolyl) pentene-2 were produced. The yield was thus 94%.

Comparative Example 1

Preparation of a catalyst and production of a monoalkenyl benzene were carried out in the same way as in Example 1 except that precursor of the catalyst was used as a catalyst without being subjected to the contacting treatment with ethanol.

Analysis revealed that the yield of 5-(o-tolyl) pentene-2 was 79%.

Comparative Example 2

To 30 g of potassium carbonate dried at 500° C. for 5 hours, 6 g of sodium were added under a nitrogen atmosphere, and the resulting mass was agitated vigorously at 200° C. in order to deposit sodium on the potassium carbonate support for producing a catalyst. The produced catalyst, which was pasty in its entirety at 200° C., was solidified into the form of wax in its entirety when allowed to cool to room temperature.

Comparative Example 3

1 g of sodium was deposited on 50 g of the potassium carbonate employed in Comparative Example 2 in the same way as in Comparative Example 2 for preparing a catalyst. Unlike the catalyst obtained in Comparative Example 2, the catalyst produced was purplish in color and excellent in dispersibility. Reaction was carried out in the same way as in Example 1 except employing 15 g of the above catalyst. As a result, 5-(o-tolyl) pentene-2 was produced with a yield of 27%.

Example 3

Preparation of a catalyst and production of a monoalkenyl benzene were carried out in the same way as in Example 1 except that p-xylene was employed as the alkyl benzene in place of o-xylene. As a result, 5-(p-tolyl) pentene-2 was produced with a yield of 75%.

Example 4

Preparation of a catalyst and production of a monoalkenyl benzene were carried out in the same way as in Example 1 except that ethyl benzene was employed as the alkyl benzene in place of o-xylene and the scale for the catalyst and the reagents was set to ½. As a result, 5-phenylhexene-2 was produced with a yield of 52%.

Example 5

Preparation of a catalyst and production of a monoalkenyl benzene were carried out in the same way as in Example 1 except that 1,3-pentadiene (90% purity; cis/trans=23.4/76.6) was employed as the conjugated diene compound in place of 1,3-butadiene. As a result, a mixture of 1-(o-tolyl) hexene-3 and 4-methyl-5-(o-tolyl) pentene-2 was produced with a yield of 77%.

Example 6

180 g of potassium hydroxide and 234 g of aluminum hydroxide (both manufactured by WAKO PURE CHEMICAL INDUSTRIES, LTD.) were calcined in a muffle furnace at 1200° C. for 5 hours. The calcined product was ground in a centrifugal ball mill for 2 hours, and the powdered product having the particle size of less than 60 mesh were selected and used as a support. This support had the composition of $K_2O.1.1Al_2O_3$.

60 g of the support thus obtained were heated to 200° to 220° C. in the same apparatus as in Example 1. To the heated mass were added 6 g of sodium under agitation. After the end of the addition, the agitation was continued for 3 hours to give a precursor of a catalyst. The produced precursor was in the form of powders which were purplish in color and excellent in dispersibility.

16 g of the precursor produced above were introduced into a mixed solution of 300 g of o-xylene and 2.9 g of ethanol, agitated for 30 minutes, and washed with o-xylene, thereby obtaining a catalyst. In this operation, the amount of ethanol equivalent in mole to the amount of sodium was consumed in the contacting reaction.

o-Xylene and 1,3-butadiene were reacted in the same way as in Example 1 except using the thus obtained catalyst. As a result, 5-o-(tolyl) pentene-2 was produced with a yield of 89%.

Example 7

Preparation of a catalyst and production of a monoalkenyl benzene were carried out in the same way as in Example 6 except that a mixed solution of 1000 g of o-xylene and 5.8 g of ethanol was employed in place of the mixed solution of 300 g of o-xylene and 2.9 g of ethanol. The amount of ethanol equivalent in mole to twice the amount of the sodium was consumed in the contacting reaction. As a result, 5-o-(tolyl) pentene-2 was produced with a yield of 90%.

Example 8

Preparation of a catalyst and production of a monoalkenyl benzene were carried out in the same way as in Example 1 except that methanol was employed in place of ethanol. As a result, 5-o-(tolyl) pentene-2 was produced with a yield of 85%.

Example 9

Preparation of a catalyst and production of a monoalkenyl benzene were carried out in the same way as in Example 1 except that isopropyl alcohol was employed in place of ethanol. As a result, 5-o-(tolyl) pentene-2 was produced with a yield of 86%.

Example 10

16 g of the precursor of a catalyst produced in the same way as in Example 6 were introduced into a mixed solution of 100 g of o-xylene and 390 mg of ethylene glycol, agitated for 30 minutes, and washed with oxylene, thereby obtaining a catalyst. In this operation, the amount of ethylene glycol equivalent to 10 mol % of the sodium was consumed in the contacting reaction.

The catalyst obtained above was charged in an autoclave in its entirety, and 425 g of o-xylene and 54 g of 1,3-butadiene were added thereto. The reaction was carried out at 140° C. for 2 hours. As a result, 5(o-tolyl) pentene-2 was produced with a yield of 75%.

Example 11

16 g of the precursor of a catalyst produced in the same way as in Example 6 were introduced into 680 g of o-xylene containing 0.01 wt % of water, and agitated for 1 hour to obtain a catalyst. In this operation, the amount of water equivalent to 6 mol % of the sodium was consumed in the contacting reaction.

o-Xylene and 1,3-butadiene were reacted in the same way as in Example 10 except using the catalyst thus obtained. As a result, 5-o-(tolyl) pentene-2 was produced with a yield of 76%.

Example 12

138 g of anhydrous potassium carbonate and 78 g of aluminum hydroxide were adjusted to have a uniform particle size each of smaller than 16 meshes and mixed together sufficiently uniformly. The resulting mixture was calcined at 1300° C. for 5 hours to prepare a support. The K/Al ratio of the support was determined by atomic absorption spectrometry to be K/Al=2. That is, the composition of the support was $K_2O.0.5Al_2O_3$.

15 g of the produced support and 1.5 g of sodium were charged into a stainless steel autoclave of 1000 ml capacity, into which 30 g of liquid ammonia were introduced under pressure and reaction was carried out at room temperature under agitation for 2 hours. After the end of the reaction, hydrogen yielded by the reaction between ammonia and sodium and ammonia were released to the atmosphere. Through this reaction, a precursor of a catalyst wherein sodium amide was supported on the support was produced.

Into the autoclave in which this precursor had been produced, 100 g of o-xylene was charged, and a mixed solution of 50 g of o-xylene and 600 mg of ethanol was further added thereto little by little over 1 hour under agitation. In this operation, the amount of ethanol equivalent to 20 mol % of the sodium amide was consumed in the contacting reaction.

After o-xylene was removed from the reactor by vacuum distillation, 425 g of fresh o-xylene and 43 g of 1,3-butadiene were added, and the reaction was carried out at 140° C. for 2 hours. As a result, 5-(o-tolyl) pentene-2 was produced with a yield of 83%.

Example 13

Aluminum hydroxide and potassium hydroxide (both manufactured by WAKO PURE CHEMICAL INDUSTRIES, LTD.) were weighed at the same ratio as in Example 6. To the resulting mixture was added a minor amount of water and kneaded together. The resulting mass was extruded by a molding machine to give an extruded product having a diameter of 1.6 mm 0. The resulting extruded product was dried at 150° C. for 1 hour and calcined at 900° C. for 8 hours in a furnace. The resulting calcined product was fractured to pieces each about 3 to 5 mm long, and used as a support.

To the thus, obtained support was added sodium at 200° C. under a nitrogen atmosphere so that sodium in a precursor of a catalyst to be obtained accounted for 10 wt %, and the mixture was agitated slowly for 2 hours for supporting sodium on the support. The agitated mixture was heated to 400° C. and agitated for another 2 hours under heating to give a precursor of a catalyst.

30 g of the thus obtained precursor was introduced into a mixed solution of 150 g of o-xylene and 1.1 g of ethanol, agitated for 30 minutes, and washed with oxylene, thereby obtaining a catalyst. In this operation, the amount of ethanol equivalent to 20 mol % of sodium was consumed in the contacting reaction.

The catalyst thus obtained was charged under a nitrogen atmosphere into a center segment of a reaction tube (inner diameter: 30 mm φ, length: 500 mmL) of a stainless steel continuous flow type reactor with a fixed bed for reaction of o-xylene and 1,3-butadiene. o-Xylene and 1,3-butadiene were charged into a tank for starting materials at a molar ratio of 10:1, and then introduced into the reactor by a pump for reaction. The reactor was maintained at 140° C. under 20 kgf/cm$^2$, and the starting material mixture was introduced at a liquid hourly space velocity (LHSV) of 1.0 hr$^{-1}$. The reaction rate of 1,3-butadiene reached 95% in three hours after start of the reaction. The half-value period of catalytic activity, i.e. the time required until the reaction rate of 1,3-butadiene was decreased by one-half from its maximum value, was 1500 hours or more. The reaction liquid recovered was freed of unreacted 1,3-butadiene, and subsequently o-xylene was recovered in a distillation column for reuse. Then the objective 5-(o-tolyl) pentene-2 was recovered under vacuum distillation. It was found that there was substantially no bottom residue in the distillation column and it was shown that high-boiling products were hardly produced.

Example 14

200 g of potassium hydrogen carbonate and 101 g of γ-alumina were mixed thoroughly, and calcined at 1000° C. for 7 hours to give a support. The support had the composition of $K_2O.1.0Al_2O_3$. 1.5 g of sodium were added to 15 g of the produced support, and agitated at 200° C. for 1 hour for depositing sodium on the support to give a precursor of a catalyst. The produced precursor was charged in its entirety into an autoclave of 1000 ml capacity. 100 ml of n-heptane as a solvent was charged into the autoclave, and the temperature was raised to 160° C. Pressure was raised with hydrogen to 70 kg/cm$^2$ G and agitation was carried out for 3 hours. Pressure decrease during this time was 2.5 kg/cm$^2$.

After cooling, residual hydrogen was discharged. The precursor thus treated was introduced into a mixed solution of 100 g of o-xylene and 600 mg of ethanol, agitated for 30 minutes, and washed with o-xylene, thereby obtaining a catalyst. In this operation, the amount of ethanol equivalent to 20 mol % of sodium was consumed in the contacting reaction.

o-Xylene and 1,3-butadiene were reacted in the same way as in Example 10 except using the catalyst thus obtained. As a result, 5-o-(tolyl) pentene-2 was produced with a yield of 80%.

Example 15

11.2 g of t-butoxy potassium and 24.6 g of aluminum-sec-butoxide were charged into 200 ml of t-butanol, and mixed at 70° C. under a nitrogen atmosphere. K(Al(OC(CH$_3$)$_3$))(OCH(CH$_3$)CH$_2$CH$_3$)$_3$), an ate-complex, was precipitated as a white-tinted precipitate. After the solvent t-butanol was distilled off under vacuum, the resulting precipitate was pre-calcined in a nitrogen stream at 500° C. for 4 hours for decomposing the organic residues in their entirety. The temperature was raised to 1200° C. and calcining was further continued for 3 hours to give a support.

To 15 g of the produced support were added 1.5 g of sodium under a nitrogen stream, and the mixture was agitated at 200° C. for 2 hours to deposit sodium on the support, thereby obtaining a precursor of a catalyst.

Preparation of a catalyst and reaction of o-xylene and 1,3-butadiene were carried out in the same way as in Example 1 except using the obtained precursor of a catalyst and 1.23 g of phenol in place of ethanol. As a result, 5-(o-tolyl) pentene-2 was produced with a yield of 86%.

Example 16

Preparation of a catalyst and production of a monoalkenyl benzene were carried out in the same way as in Example 14 except that potassium was employed in place of sodium. As a result, 5-o-(tolyl) pentene-2 was produced with a yield of 82%.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A method for producing a monoalkenyl benzene comprising reacting an alkyl benzene having 7 to 10 carbons with a conjugated diene compound having 4 to 6 carbon atoms in the presence of a catalyst, wherein said catalyst is prepared by
   (1) preparing a catalyst precursor by depositing at least one component selected from the group consisting of sodium, potassium, sodium amide, and potassium amide on a support consisting essentially of a compound represented by the formula $K_2O \cdot xAl_2O_3$ wherein x is $0.5 \leq x \leq 11$; and
   (2) contacting said precursor with at least one of water, an alcohol, and a phenol represented by the formula $R^7OH$, wherein $R^7$ is an aryl group having 6 to 20 carbon atoms.

2. The method as claimed in claim 1 wherein said support is produced by contacting a potassium-containing compound with an aluminum-containing compound.

3. The method as claimed in claim 2 wherein said potassium-containing compound is selected from the group consisting of potassium hydroxide, potassium hydrogen carbonate, potassium carbonate, potassium hydride, potassium acetate, methylpotassium, vinylpotassium, ethylpotassium, phenylpotassium, tolylpotassium, benzylpotassium, dodecylpotassium, hexadecylpotassium, dimethyl benzylpotassium, phenyl ethylpotassium, ethoxypotassium, butoxypotassium, isopropoxypotassium, and mixtures thereof.

4. The method as claimed in claim 2 wherein said aluminum-containing compound is selected from the group consisting of hydrargillite, nordstrandite, bayerite, boehmite, diaspore, α-alumina, θ-alumina, κ-alumina, δ-alumina, η-alumina, γ-alumina, χ-alumina, ρ-alumina, trimethoxy aluminium, triethoxy aluminum, tripropoxy aluminum, triisopropoxy aluminum, tributoxy aluminum, triisobutoxy aluminum, tri-sec-butoxy aluminum, tri-tert-butoxy aluminum, tripentyloxy aluminum, triisopentyloxy aluminum, trineopentyloxy aluminum, tri-tert-pentyloxy aluminum, trihexyloxy aluminum, triisohexyloxy aluminum, triheptyloxy aluminum, trioctyloxy aluminum, triphenoxy aluminum, tribenzyloxy aluminum, and mixtures thereof.

5. The method as claimed in claim 1 wherein said component is present in an amount of 0.1 to 30 parts by weight based on 100 parts by weight of said support.

6. The method as claimed in claim 1 wherein said precursor is contacted with hydrogen before said contacting with at least one of water, an alcohol, and a phenol.

7. The method as claimed in claim 6 wherein said precursor is contacted with said hydrogen at a temperature of 0° to 400° C. under the pressure of 0 to 100 $kg/cm^2 \cdot G$.

8. The method as claimed in claim 1 wherein said alcohol is selected from the group consisting of methanol, ethanol, 1-propanol, 2-propanol, 1-butanol, 2-butanol, 2-methyl-1-propanol, 2-methyl-2-propanol, 1-pentanol, 2-pentanol, 3-pentanol, 1-hexanol, 1-heptanol, 1-octanol, benzyl alcohol, α-methylbenzyl alcohol, phenethyl alcohol, ethylene glycol, propylene glycol, glycerol, and mixtures thereof.

9. The method as claimed in claim 1 wherein said phenol is selected from the group consisting of phenol, cresol, naphthol, and mixtures thereof.

10. The method as claimed in claim 1 wherein said at least one water, alcohol, and phenol is present in an amount of 0.1 to 200 mol % of said at least one component in said precursor.

11. The method as claimed in claim 1 wherein said contacting is carried out in a liquid hydrocarbon as a solvent.

12. The method as claimed in claim 11 wherein said liquid hydrocarbon is selected from the group consisting of heptane, octane, nonane, decane, undecane, dodecane, decalin, toluene, ethylbenzene, xylene, diethylbenzene, trimethylbenzene, cumene, ethyldimethylbenzene, cymene, and mixtures thereof.

13. The method as claimed in claim 1 wherein said contacting is carried out at −10° to 50° C. for 10 minutes to 10 hours.

14. The method as claimed in claim 1 wherein said catalyst is in a form of a pellet.

15. The method as claimed in claim 1 wherein said alkyl benzene having 7 to 10 carbon atoms is selected from the group consisting of toluene, ethyl benzene, xylene, diethyl benzene, trimethyl benzene, cumene, ethyldimethyl benzene, cymene, tetramethyl benzene, and mixtures thereof.

16. The method as claimed in claim 1 wherein said conjugated diene compound is selected from the group consisting of 1,3-butadiene, isoprene, 1,3-pentadiene, 2,3-dimethyl butadiene, 2-ethyl butadiene, 2-methyl-1,3-pentadiene, 3-methyl-1,3-pentadiene, 4-methyl-1,3-pentadiene, 1,3-hexadiene, 2,4-hexadiene, and mixtures thereof.

17. The method as claimed in claim 1 wherein a mixing ratio of said alkyl benzene having 7 to 10 carbon atoms to said conjugated diene compound having 4 to 6 carbon atoms is 1:0.001 to 0.5 in molar ratio.

18. The method as claimed in claim 1 wherein said reacting of the alkyl benzene having 7 to 10 carbon atoms with the conjugated diene compound having 4 to 6 carbon atoms is carried out at 80° to 200° C. under the pressure of 5 to 200 $kgf/cm^2$.

* * * * *